United States Patent [19]
Rudt et al.

[11] Patent Number: 5,821,990
[45] Date of Patent: *Oct. 13, 1998

[54] SYSTEM FOR MONITORING A CONTINUOUS MANUFACTURING PROCESS

[75] Inventors: Robert J. Rudt, Highland Mills, N.Y.; Leonard F. Fiore, Foley, Minn.; Kenneth D. Grapes, Indian Springs, Ohio

[73] Assignee: Champion International Corporation, Stamford, Conn.

[*] Notice: The term of this patent shall not extend beyond the expiration date of Pat. No. 5,717,456.

[21] Appl. No.: 929,231

[22] Filed: Sep. 3, 1997

Related U.S. Application Data

[62] Division of Ser. No. 399,235, Mar. 6, 1995, Pat. No. 5,717,456.

[51] Int. Cl.$^6$ .................................................. H04N 7/18
[52] U.S. Cl. .............................. 348/88; 348/86; 348/125
[58] Field of Search ................................ 348/88, 86, 125, 348/92, 94, 128; 356/429, 430, 240; 382/141

[56] References Cited

U.S. PATENT DOCUMENTS

| | | | |
|---|---|---|---|
| H1616 | 12/1996 | Wolfe | 348/88 |
| 4,675,730 | 6/1987 | Adomaitis et al. | 348/88 |
| 4,752,897 | 6/1988 | Zoeller et al. | 364/550 |
| 4,805,019 | 2/1989 | Holliday | 348/86 |
| 4,951,223 | 8/1990 | Wales et al. | 364/507 |
| 5,023,714 | 6/1991 | Lemelson | 348/88 |
| 5,134,574 | 7/1992 | Beaverstock et al. | 364/551.01 |
| 5,239,376 | 8/1993 | Dittmann et al. | 348/88 |
| 5,305,099 | 4/1994 | Morcos | 348/88 |
| 5,365,596 | 11/1994 | Dante et al. | 348/125 |
| 5,680,473 | 10/1997 | Kanzaka et al. | 382/141 |
| 5,717,456 | 2/1998 | Rudt et al. | 348/88 |

FOREIGN PATENT DOCUMENTS

| | | | |
|---|---|---|---|
| WO 93/05477 | 3/1993 | WIPO | G06F 11/22 |
| WO 94/11821 | 5/1994 | WIPO | G06F 15/40 |

*Primary Examiner*—Tommy P. Chin
*Assistant Examiner*—Vu Le
*Attorney, Agent, or Firm*—Richard C. Stewart, II

[57] ABSTRACT

A system for continuously monitoring a process such as a paper making process wherein a plurality of video cameras are positioned at various positions along the process to monitor one or more pre-determined characteristics of the process. The system further includes device for converting the monitored characteristics into digital format and a digital data storage device, such as a circular memory, for storage of such data such that as new data is stored earlier stored data is removed. The system includes a control device such as a computer which is capable of communicating with the data storage device and with a detector for detecting deviations from the monitored predetermined characteristic such that on receipt of a deviation signal the control device extracts from the digital data storage device digitized data corresponding to the deviation and displays such extracted deviation digitized data as for example on a video monitor.

66 Claims, 1 Drawing Sheet

SYSTEM FOR MONITORING A CONTINUOUS MANUFACTURING PROCESS

This is a division of application Ser. No. 08/399,235, filed Mar. 6, 1995 pending.

BACKGROUND OF THE INVENTION

1. Field of the Invention

This invention relates generally to a system for monitoring a process. More particularly, this invention relates to such a system in which process data relating to a predetermined characteristic of the process is collected and stored in digital format and extracted based upon a predetermined criterion for display.

2. Description of the Prior Art

Processes are known for the continuous production or handling of a product. Illustrative of such processes are those for the production or handling of continuous products, as for example polymeric films, paper webs, metallic webs, roll printing processes and the like. Other such processes include those for production or handling of discrete products such as sheet printing processes, packaging processes and the like.

A desired objective of these processes is that the product have certain pre-determined characteristics, as for example characteristics which insure that the product is of acceptable quality. A failure to detect and correct deviations from these pre-determined characteristics is an extreme disadvantage adversely affecting the economics of the process as for example because of lost production time, discarding of unacceptable product, and the like.

As a result, systems for inspecting and observing the product by continuous processes have been developed. See for example the systems described in U.S. Pat. Nos. 4,951,223; 4,814,869; 5,239,376; and the like. These systems usually involve the monitoring through use of one or more video cameras strategically placed along the production line, storage of video output on video tapes, means for shutting down production of the product in the event of deviations from pre-determined characteristics and playback of video tapes to determine the cause of the deviations so that corrections can be made in a timely fashion. These known monitoring systems suffer from one or more disadvantages which adversely affect their performance. For example, these prior processes are manual and require re-winding of the tape which results in down time of the system and long processing times. Moreover, tapes often degrade and it is difficult to access those portions of the tape containing relevant information or to make good copies. In these systems the tapes are not networked or tied together and the system cannot simultaneously recorded and played back. The system of this invention obviates one or more of these disadvantages.

SUMMARY OF THE INVENTION

This invention provides a monitoring system for continuously monitoring the operations of a machine for the continuous manufacture of a product. More particularly, the system of this invention comprises:

a plurality of monitoring means for continuously monitoring a pre-determined characteristic of the process and collecting monitored data, each monitoring means addressing a different location of interest of said process, and capable of monitoring and collecting real time data relative to said location;

data converting means for converting said output data into digitized data;

digital data storage means capable of storing segments of said digitized data, each of said segments comprised of a plurality of digitized data clips, said segments and said clips of predetermined lengths which cover the operations of said process at a relevant location over a predetermined period of time, said digitized data segments being stored such that as new digitized data is stored in said segment, the earliest prior stored digitized data in said segment is displaced from said segment to maintain said segment at said predetermined length; and control means for controlling said monitoring system, said control means in communication with said digital data storage means and capable of extracting one or more digitized data clips according to predetermined criterion to form one or more extracted clips, and capable of displaying said extracted clips.

As used herein, "compression" means applying data reduction means such as an appropriate algorithim, technique, technology or the like to digitalized data for a real time event at a location in a process to reduce the ammout of digitized data required to recreate the event. As used herein, "process" means an action, change or function or a series of actions, changes or functions that bring about a result or end, as for example a system of operations in the production of something. As used herein, "clip" means a digitalized data series for a location of a process during a pre-determined period of time. As used herein, "digitized" or "digitization" means to convert to or to collect in a digital format as for example conversion of an analog signal of a visual image to a digital format or collection of a visual image directly into a digital format. As used herein, "digital" means information in a binary format, or zeros and ones, usual for storage in a digital data storage means such as a computer. As used herein, "segment" means a portion of the digital data storage means containing one or more digitized data clips.

In a preferred embodiment of the invention, said process is a continuous process for the manufacture of a product, and said deviation event is a deviation in a pre-determined characteristic of said product.

In a more preferred embodiment of the invention, the system comprises a plurality of storage means, each of which comprises at least one digitized data segment, at least one of said storage means capable of storing digitized data monitored and collected from first monitoring means at a first location of the process and at least one of said storage means capable of storing data monitored and collected from a second monitoring means at a second location of the process. Preferably, the control means is capable of extracting clips from segments stored in two or more of said plurality of said storage means such that said extracted clips are time synchronized to chronologically show the predetermined characteristic of a single discrete product or a portion of a continuous product as said product passes by each location of the digitized data in said extracted clips. Alternatively, the control means is capable of extracting the event clip recording said event and the clip immediately preceding said event clip from the segment containing data from a single location of the process, and optionally the data clip immediately following the event clip, splicing said clips in chronological order to form a display clip and displaying said display clip.

In another preferred embodiment, the process comprises a plurality of steps and wherein there is at least one monitoring means, data converting means and data storage means for said step.

In still another preferred embodiment, the process is controlled by a distributive control system in communication with said control means, said control system having one or more deviation detectors for monitoring said pre-determined characteristic, each of said detectors addressing a different location of interest along the process and capable of detecting deviation events and communicating a signal of said deviation event, and the time and location of said event to said control means;

wherein on receipt of said deviation event signal said control means capable of identifying data storage means containing the digitized data segment corresponding to said deviation event, extracting the deviation event clip and displaying said display clip, and wherein said distributive control system is preferably capable of communicating process data relating to the operation of the process and the time of break to said control means.

In yet another preferred embodiment, the control means is capable of extracting the event clip recording said event and the clips immediately preceding and optionally the clip immediately following said event clip, splicing said clips into a display clip chronological order and displaying said display clip.

A most preferred embodiment of this invention relates to a monitoring system for monitoring the manufacture of a continuous web of paper having one or more pre-determined characteristics in a paper manufacturing machine comprising:

a plurality of monitoring means which comprises one or more video cameras for monitoring the paper web, each monitoring means addressing the paper web at a different location of interest along the paper manufacturing machine and capable of producing a video image of the paper web at the location;

digital converting means for converting the video image into a digitized video signal;

digital data storage means capable of receiving said digitized video signal and storing digitized segments thereof, each of which comprises a plurality of digitized clips, said digitized segments and clips of a predetermined length covering real time operation of said machine, said digitized segments being stored such that the earliest prior stored digitized data in said segment is displaced as new digitized data, is stored in said segment to maintain said stored segment at said predetermined length;

Computer control means for controlling the operations of said system, said means in communication with said digital data storage means and capable of controlling same, said computer control means in communication with a distributive control system for controlling said machine, said system having one or more deviation detectors for detecting deviations from predetermined characteristics as said paper web passes through said machine said control system capable of communication process master time and date information to said computer control system; and one or more video monitors in communication with said computer control means and capable of displaying the image of digitized video signals under the control of said computer control means;

wherein on occurrence of a deviation from the predetermined characteristics of said web, said distributive control system transmits a deviation signal comprising the time, date and location of said deviation event to said computer control means, and in response thereto said computer control means identifying the digitized data segment corresponding to said deviation event, extracting the deviation event clip, the preceding clip preceding said break event clip to form a display clip and displaying said display clip on a video monitor.

The system of this invention obviates one or more disadvantages of prior art monitoring systems. For example, There no loss or substantially no loss of data due to rewinding, no or substantially no deterioration in the stored data and good copies of the data can be made. The system can be easily used in an automatic mode an allows simultaneous observation and collection\storage of data. The system allows the monitoring of the process from a central location or from one or more other locations, and allows correlations between collected\recorded data and other process operations data.

BRIEF DESCRIPTION OF THE DRAWINGS

The invention and the advantages attendant thereto will become apparent upon a reading of the following detailed description of the invention taken in conjunction with the accompanying drawings, in which.

DETAILED DESCRIPTION OF THE INVENTION

Figure 1:
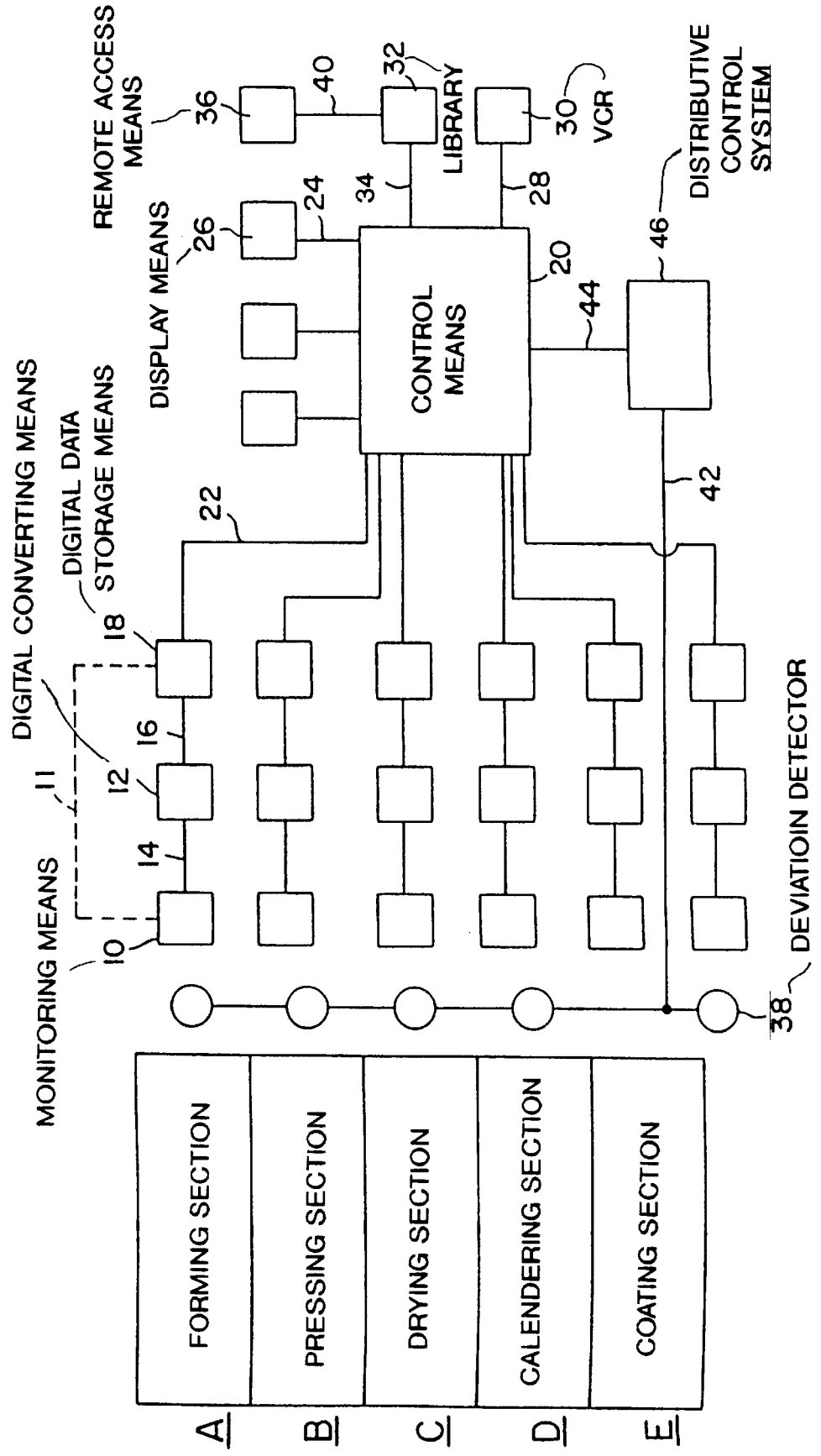
FIG. 1 is a depiction of a preferred embodiment of this invention showing a schematic of a paper making machine, including a possible configuration of surveillance cameras and web failure detection devices.

The present invention is directed to a system for monitoring a machine or process for manufacture of a product. While the preferred embodiment of FIG. 1 depicts the system in use to monitor a paper manufacturing process and machine. The nature of the process may vary provided that the process has a pre-determined characteristic. The process may be batch, semi-continuous or continuous, or automatic or manual. For example, the process may monitor people or things entering or leaving a building or a room in a building or a process for the manufacture or handling of discrete or continuous products. In the preferred embodiments of the invention, the process is for the manufacture or handling of a product. Processes for manufacturing and handling discrete products include processes for extruding, packaging, filing, bottling, sheet fed printing, conveying, converting, wrapping, stamping, or assembling a discrete product. Process for manufacturing or handling a continuous product include those for the manufacture of a continuous web material such as a polymeric or metal sheet or film, printed paper, carpet, woven material, non-woven material, textile material or photographic film which has certain predetermined characteristics which must not be deviated from. The system can be conveniently used to monitor the manufacture of such continuous or discrete products to monitor for any deviations from the desired pre-determined characteristic(s).

The system is especially useful in paper manufacture as depicted in more detail in FIG. 1. FIG. 1 depicts a schematic representation of a paper making machine in which the wet end forming section is at the top and the final product section is at the bottom. As depicted in the figure, the machine consists of five sections, denoted by A, B, C, D and E. A denotes the forming section; B denotes the pressing section; C denotes the drying section; D denotes the calendaring section; and E denotes the coating section. As shown on FIG. 1, monitoring means 10 are strategically positioned at various locations of interest along the paper making machine.

Observing means 10 may vary widely and depends on a pre-determined characteristic of the product being monitored for deviation events. Illustrative of useful observing means are those which employ coherent or non-coherent visual, gamma, infra-red, ultraviolet, thermal and nuclear radiation, sonics, ultrasonics, magnetic fields, pressure, odor and the like. The particular observing means 10 used in any particular situation will normally depend on the pre-determined characteristics of the product being observed and the event which indicates a deviation from the pre-determined characteristic. For example, if the pre-determined characteristic is continuity of the web of paper and the deviation is a break or hole in the web, then monitoring means which employs visual radiation such as a video camera can be conveniently employed. On the other hand, if the pre-determined characteristics are moisture content, surface texture, color, gloss and the like monitoring means which involve the use of visual and infrared radiation may be used.

In the preferred embodiment of this invention depicted in FIG. 1, monitoring means is a plurality of video cameras 10. While seven cameras 10 are depicted in the figure, the number of cameras employed may vary widely, and any number capable of providing the desired degree of monitoring can be employed. The positioning of various monitoring means 10 may vary widely depending on the needs of the user. In the preferred embodiment depicted in FIG. 1, where the pre-determined characteristic of the web being monitored is web continuity and deviations in this characteristic being detected are break events, hole events or a combination thereof, the number of cameras 10 and camera positions are such that locations where breaks are most likely to occur are covered. For example, as depicted in FIG. 1, cameras 10 are positioned at the drawing section, coating section, size pressing section, center rolls section, sheet pick-up section and reeling device section.

The system of this invention also includes digital converting 12 means for converting data obtained or generated by monitoring means 10 into a digital format. Digital converting means employed may vary widely and any such means capable of performing this function may be used. Illustrative of suitable digital converting means 12 are electronic circuit boards, converting signal processors, video boards, micro-chips, and assorted software. The number of digital converting means 12 and the relationship of digital converting means 10 to monitoring means 10 may vary widely, the only requirement is that relevant monitored data is eventually converted into digital format. For example, there may be a single digital converting means 12 for each monitoring means 10 or there may be one or more digital converting means 12 for all monitoring means 10 or various other combinations of converting means 12 and monitoring means 10 may be employed. Digital converting means 12 and monitoring means 10 may be separate devices as depicted in FIG. 1, or these functions may be performed by the same device as for example a digital video camera 10 which directly monitored data in a digital format, which data is conveyed directly to digital data storage means 18 via conductor 11.

As depicted in FIG. 1, each video camera 10 monitors the web and monitored data is generated in an analog format. The analog data is then conveyed to digital converting means 12 via conductor 14 where the analog data is converted to digital format by digital converting means 12, with or without data compression. The digitized data is then conveyed via conductor 16 to digital data storage means 18.

The specific digital data storage means 18 may vary widely provided that such means allows storage of segments of digitized data having a pre-determined length which covers data obtained by monitoring means 10 which cover the real time operations of the machine over a predetermined period of time. The segment, in turn, is comprised of a plurality of digitized data clips which are also of a pre-determined length which also cover the real time operations of the machine over a predetermined period of time. The segments and clips are in chronological order and are preferably identified by date and time at which the data was collected which greatly facilitates access to relevant data clips on occurrence of a deviation event. Preferably, the clips are also stored such that clips can be readily identified by time and date, and can be extracted or copied from the segment. A further requirement of the digital memory storage means 18 is that it can be controlled by a control means 20 such that specific clips can be extracted from the digital data storage means 18 as desired and as will be described hereinbelow in more detail. In the operations of the digital data storage means 18, the segment is maintained at or about the pre-determined length during the operations of the system such that as new digitized real time data is added to digital data storage means 18, the oldest or most prior data is erased, deleted or otherwise removed from storage means 18 maintaining said segment at or about some pre-determined length. The advantages of this storage means 10 becomes readily apparent in that stored digital data showing normal operations to produce the product having the pre-determined characteristic is constantly removed from storage means 18 such that upon storage of deviating digitized data of a deviation from the pre-determined characteristic, as for example a break event, such deviating data can be more easily isolated from the relatively small amount of data comprising the segment.

The pre-determined length of the segment and the clips may vary widely initially and during the operation of the system, usually depending upon function and capacity of the digital data storage means, duration of the deviation event and the like. The length of the segments are preferably less than about 60 minutes, more preferably from about 15 to about 60 minutes, and most preferably from about 15 to about 30 minutes. The length of the clips comprising a segment is preferably less than about 60 secs., more preferably from about 5 to about 60 secs., more preferably from about 5 to about 20 to 30 secs and most preferably from about 5 to about 10 secs.

The digitized data storage means 18 utilized in any particular situation may vary widely. Illustrative of useful data storage means 18 are hard drive, tape, diskette, CD rom, magnetic optical drive, solid state memory, flash memory, optical device, and the like. Preferred digitized data storage means 18 are hard drives and CD roms. As depicted in FIG. 1, the most preferred digitized data storage means 18 is a hard drive and is in communication with control means 20 by way of connector 22. Control means 20 functions to control the system. Useful control means 20 may vary widely, the only requirement is that means 20 is in the event of a deviation event able to locate the data clip containing data of such event, to extract such data clip and to display said data clip. Illustrative of useful control means 20 are analog control system and a digital computer.

As depicted in FIG. 1, control means 20 is a digital computer which communicates via connector 24 to a plurality of display means 26 which in the embodiment of FIG. 1 are video monitors. Useful display means 26 may vary widely the only is that such means is capable of displaying data to the satisfaction of the operator. Other useful display means 26 are printers, projection systems, photographic imagers and the like. Also connected to control means 20 by way of cable 28 is a video recorder 30 as for example a VCR for recording for wider distribution of data and a library 32 for storage of data by way of cable 34. As depicted in the figure, library 32 can be accessed from various locations by remote access means 36 such as a local area network, wide area network, e-mail services, satellite, compact disk and the like connected to library 32 via cable 40.

FIG. 1 also depicts a plurality of deviation detectors 38 strategic positioned along the machine in a well known manner to detect deviations in the pre-determined characteristics in the product being monitored. Detectors 38 are connected to the machine control or distributive control system 46 via cable 42 for transmission of a deviation signal to system 46. System 46 also communicates with control 20 via cable 44 such that various information can be transmitted to control 20 from system 46 in the event of a deviation from the pre-determined characteristic as for example a break in a web. Such information includes the detection of a deviation event, time of detection of the deviation event and such other process data relating to the operations of the machine at the time of deviation event deemed appropriate.

In operation, monitoring means 10 continuously monitors a pre-determined characteristic of the product being produced by the machine. The monitored data is conveyed via cable 14 to digital conversion means 12 where the data is converted to a digital format, and the digitized data is conveyed to digital data storage means 18 via cable 16 for storage. In those embodiments of the invention where the monitored data is collected in digital format by monitoring means 10, as for example by a digital video camera, the digitized data is converted directly to digital data storage means 18 via cable 11. During operations where there are no deviations from the pre-determined characteristics, digitized data flows continuously into storage means 18 such that only a pre-determined amount of data converting a pre-determined period of time during the operation of the machine is always maintained in storage and that as new data is stored the oldest or most prior data is deleted or erased.

If a deviation in the pre-determined characteristics of the product occurs, it is detected by a deviation detector 38. Detector 38 sends a deviation signal to distributive control system 46 via cable 42, and the signal is relayed to control means 20 via cable 44. In addition to a deviation signal, detector 38 may also inform control system 46 of the identity of detector 38 detecting the deviation event, the time of the deviation event and location in the process of the deviation event. This information together with other process data such as type of product being manufactured, machine operation parameters, machine speed, draw ratios, furnish, types, additives, coating components, calendaring pressures, coating thickness, basis weight of the paper and the like are conveyed to control means 20. On receipt of the deviation event signal, control means 20 is capable of identifying the clip most likely to have digitized data relating to the deviation event, and extracting such clip and displaying the extracted clip with display means 26. For example, control means 20 can perform this function by coordinating the time at which deviation event detector 38 detected the deviation event with the clip or clips corresponding in time. This coordination can be done in any suitable manner. For example, control 20 can scan all digitized data storage means 18, select clips from all means 18 containing data collected at the appropriate time and can then scan each clip to identify the deviation event and display same. Alternatively, control means 20 can identify the monitoring means 10 most proximate to the location of the deviation event, select a clip or clips from the digitized data storage means 18 for such monitoring means 10 and display such clip. In order to insure that all suitable data is displayed in the fastest possible time, preferably control means 20 will also extract digitized data clips immediately preceding and following the clip or clips most likely containing data for the deviation event and will splice the deviation event clip and the following and preceding clips into a display clip for display. By splicing the event, preceding and following clips, the operation of the machine prior to, during and subsequent to the deviation event can be observed. After a deviation is detected, the machine is usually stopped and the digitized data storage means 18 is frozen to prevent loss of critical data.

The clips can be displayed automatically or manually at any suitable speed. The clips can be displayed frame by frame, in various sizes. The clips can also be viewed in reversed mode. This function combined with a pause, playback and resizing can enhance the ability of the operators to locate the exact point of interest on the display clip, for study showing the deviation event as it occurred. Of course, many other functions may be provided by control means 20 including zooming, edge enhancement, image sharpening, gradient edge enhancement, de-specking, filtering, cropping, desizing, dithering, interpolation, image intensity, format conversion, color inversion, contrast control, brightness control, embossing and the like. Manual/automatic control of all functions may be provided.

In this manner, the control means 20 becomes the driver which also manages the logistics of the system including monitoring, displaying, storage, etc., and can additionally be used to supervise the status of each device in the system as desired. In addition, other peripherals can be provided as needed.

The ability to review the critical period just prior to the deviation event at any desired speed provides the input necessary to evaluate the cause of the problem so that necessary adjustments and/or repairs can be started quickly and the machine restored to normal operation. If only a defect in the product is to blame, this, too, often will show up. In this manner, valuable time can be saved.

The clip or clips covering the deviation event are displayed, the cause of the deviation event can be discovered and appropriate action can be taken to correct the cause of the event. The process or machine and the monitoring system can then be reactivated.

The clips relating to the deviation event together with any other process data associated with the deviation event are conveyed via line 34 to library 32 for storage. In this manner, a collection of deviation clips and associated process data is formed which can be accessed by remote access 36 via connector 40 for suitable purposes as for example for accessing, and correlating or otherwise evaluating accessed data based on or more variables such as process times, properties, products, types or modes of deviation events, recorded observations, types of machines, and like process or product characteristics, and to document machine or process defects such as a hole in the felt or wire. The clips and associated process data may also be conveyed via connector 28 to video recorder 30 for storage on a video tape.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications both as to equipment and procedure details can be accomplished without departing from the scope of the invention.

What is claimed is:

1. A monitoring system for continuously monitoring a process comprising:
    a plurality of monitoring means for continuously monitoring a predetermined characteristic of the process and collecting monitored data, each monitoring means addressing a different location of interest of said process, and each said monitoring means for monitoring and collecting data relative to said location;
    data converting means for converting said collected data into digitized data;
    digital data storage means for storing segments of said digitized data, each of said segments comprised of one or more digitized data clips, said segments which cover the operations of said process over a predetermined period of time, said digitized data segments being stored such that as new digitized data is stored in one of said segments, earlier prior stored digitized data in said segment is removed from said segment to maintain said segment at or about said pre-determined length; and
    control means for controlling said monitoring system, said control means for communicating with said digital data storage means and for communicating with one or more deviation detectors for detecting a deviation from said predetermined characteristic and for transmitting a deviation signal of said detected deviation to said control means, wherein on receipt of said deviation signal said control means for extracting a deviation clip from said segments stored in said digital data storage means and means for displaying said extracted clip.

2. System of claim 1 wherein said process is a continuous process for the manufacture of a product, and said deviation is a deviation in a pre-determined characteristic of said product.

3. System of claim 2 wherein said process comprises a plurality of monitoring steps and wherein there is at least one monitoring means for each of said steps.

4. System of claim 1 which comprises a plurality of storage means, each of which comprises at least one of said digitized data segment, at least one of said storage means for storing digitized data monitored and collected from first monitoring means at a first location of the process and at least one of said storage means for storing data monitored and collected from a second monitoring means at a second location of the process.

5. System of claim 4 wherein each of said plurality of storage means stores digitized data monitored and collected by a single monitoring means.

6. System of claim 1 wherein a plurality of monitoring means address a single location, each in communication with a digital data converting means which is in communication with a digital data storage means, said control means for extracting one or more digitized data clips from each of said storage means and for displaying said extracted clips.

7. A system of claim 6 wherein each of said monitoring means monitors a different pre-determined characteristic.

8. A system of claim 7 wherein each of said monitoring means is different.

9. System of claim 1 wherein said process is controlled totally or in part by a distributive control system in communication with said control means, said distributive control system comprising said one or more deviation detectors, said distributive control system for communicating a signal of said detected deviation and the time, location or time and location of said deviation to said control means;
    wherein on receipt of said deviation signal said control means for identifying the stored segment containing a digitized data clip corresponding to said deviation, extracting the deviation clip to form a display clip and displaying said display clip.

10. System of claim 9 wherein said distributive control system is also for communicating process data relating to the operation of the process to said control means.

11. System of claim 10 which further comprises:
    library means in communication with said control means for storage of display clips and process data relating to the operation of the process at the time of said deviation, said library means also for providing said stored display clips and process data for display.

12. System of claim 1 wherein on receipt of said deviation signal said control means is for extracting the deviation clip recording said deviation and one or more preceding clips preceding said deviation clip in time or time and location, such that said extracted clips are time synchronized to chronologically show the predetermined characteristics as said product passes by each monitored location of the digitized data in said extracted clips, said control means for splicing said extracted clips in chronological order to form a display clip and displaying said display clip.

13. System of claim 12 wherein said control means for extracting the deviation clip recording said deviation, the clip immediately preceding said deviation clip in time or in time and location, the clip immediately following said deviation clip in time or time and location, splicing said extracted clips in chronological order to form a display clip and displaying said display clip.

14. System of claim 1 wherein said monitoring means are video cameras and wherein at least one digital converting means is in communication with at least one video camera and at least one digital data storage means is in communication with at least one digital converting means.

15. System of claim 14 wherein on receipt of said deviation signal at the time of said deviation, said control means identifies a video camera proximate to said deviation detector detecting said deviation, freezes operations of digital memory storage means for such camera, identifies the digitized data segment corresponding to said deviation by correlating the time of said segment with the time of said deviation event, extracting the deviation event clip which correlates to the time of said deviation event and the preceding clip preceding said deviation event clip and the subsequent clip following said deviation event clip, splicing said deviation event clip, said preceding clip and said subsequent in chronological order to form a display clip and displaying said display clip on said display means.

16. System of claim 15 which further comprises:
    means for transmitting process data from a distributive control system with a break event signal;
    library means for storage of display clips and associated process data; and
    means for accessing said display clips and process data stored in said library means.

17. System of claim 1 wherein said process is a continuous product and said deviation is selected from the group consisting of a break in said continuous product, a hole in said continuous product and a change in a surface characteristic of said continuous product.

18. System of claim 1 wherein each of said monitoring means and said data converting means are combined in a digital camera.

19. System for claim 1 wherein said control means is a computer.

20. System of claim 1 wherein:

a product of said process is a continuous web of paper and said process is for printing or manufacturing said web of paper;

said plurality of monitoring means comprises one or more cameras for monitoring said web of paper, each monitoring means for addressing said product at a different location of interest along said process and for producing an image of said product at the location of interest;

digital converting means for converting the image into a digitized image;

digital data storage means for receiving said digitized image and storing said digitized image in a digitized segment comprising one or more digitized images, said digitized segment of a predetermined length covering real time operation of said process, said digitized images being stored such that earlier prior stored digitized images in said digitized segment are displaced as new digitized images are stored in said digitized segment to maintain said stored digitized segment at or about said predetermined length;

computer control means for controlling the operations of said system, said computer control means for communicating with said digital data storage means and for communicating with a distributive control system for controlling all or a portion of said process, said distributive control system having said one or more deviation detectors for detecting deviations from predetermined characteristics of said product as said product passes through said process, said distributive control system for communicating to said computer control system information comprising the time, location or time and location of said deviations, information relative to said operations of said process or a combination thereof; and one or more monitors in communication with said computer control means for displaying said digitized images under the control of said computer control means;

wherein on occurrence of said deviation said distributive control system transmits said deviation signal comprising the location or time, and location of said deviation to said computer control means, and in response thereto said computer control means identifies said digitized segment or said digitized image corresponding to said deviation or a combination thereof, extracts said digitized image comprising said deviation and displays said extracted digitized image on a monitor.

21. System of claim 20 wherein each of said monitoring means and digital converting means are combined in a digital camera.

22. System of claim 1 wherein each of said monitoring means and one or more of said detectors are combined in a camera.

23. System of claim 1 wherein said deviation signal comprises the time, location or time and location of said detected deviation.

24. System of claim 23 wherein said deviation signal comprises the location of said detected deviation.

25. A monitoring system for continuously monitoring a process comprising:

a plurality of monitoring means for continuously monitoring a pre-determined characteristic of the process and collecting monitored data, each monitoring means addressing a different location of interest of said process, and each said monitoring means for monitoring and collecting data relative to said location;

digital converting means for converting said collected data into digitized data;

digital data storage means for storing segments of said digitized data, said segments of which cover the operations of said process at a relevant location over a pre-determined period of time, said digitized data segments being stored such that as new digitized data is stored in a segment, earlier prior stored digitized data in said segment is removed from said segment to maintain said segment at or about a pre-determined length; and control means for controlling said monitoring system, said control means for communicating with said digital data storage means and for communicating with one or more deviation detectors for detecting a deviation from said predetermined characteristic and for transmitting a deviation signal of said detected deviation to said control means; wherein on receipt of said deviation signal said control means for extracting from said digital data storage means deviation digitized data corresponding to said detected deviation to form extracted digitized data and said control means for displaying said extracted digitized data.

26. System of claim 25 wherein said system further comprises a monitor and wherein said extracted digitized data is displayed visually on said monitor.

27. System of claim 25 wherein on receipt of said deviation signal said control means for extracting the deviation digitized data and preceding digitized data preceding said digitized data in time or time and location such that said extracted preceding and deviation digitized data are time synchronized to chronologically show the monitored predetermined characteristics as said process passes by each monitored location of the digitized data in said extracted clips, and said control means for controlling said means for displaying said extracted clips.

28. System of claim 27 wherein said control means for extracting the deviation digitized data, the preceding digitized data, and the digitized data immediately following extracting said deviation digitized data in time or time and location and said control means for controlling said means for displaying said extracted digitized data.

29. System of claim 25 wherein said data converting means and each of said monitoring means are combined in a digital camera.

30. System of claim 25 wherein said monitoring means is a video camera.

31. System of claim 25 wherein said pre-determined characteristic is a characteristic of said process.

32. System of claim 25 wherein said control means is a computer.

33. System of claim 25 wherein:

a product of said process is a continuous web of paper and said process is a process for printing or manufacturing said web of paper;

said plurality of monitoring means comprises one or more cameras, each camera addressing said product at a different location of interest along said process and producing an image of said product at said location of interest;

digital converting means for converting the image into a digitized image;

digital data storage means for receiving said digitized image and storing said digitized image in a digitized data segment comprising one or more digitized images, said digitized data segment of a pre-determined length covering real time operation of said process, said digitized images being stored such that earlier prior stored digitized images in said digitized segment are displaced as new digitized images are stored in said digitized segment to maintain said stored digitized segment at or about said predetermined length;

computer control means for controlling the operations of said system, said computer control means for communicating with said digital data storage means and for communicating with a distributive control system for controlling all or a portion of said process, said distributive control system having said one or more deviation detectors for detecting deviations from predetermined characteristics of said product as said product passes through said process, said distributive control system for communicating to said computer control system information comprising the location or time and location of said deviations; information relative to the operations of said process or a combination thereof; and one or more monitors in communication with said computer control means for displaying the digitized images under the control of said computer control means;

wherein on occurrence of said deviation, said distributive control system transmits said deviation signal comprising the location or time and location of said deviation to said computer control means, and in response thereto said computer control means identifies said digitized segment or said digitized image corresponding to said deviation or a combination thereof, extracts said digitized image comprising said deviation and displays said digitized image on said monitor.

34. System of claim 33 wherein each of said monitoring means and digital converting means are combined in a digital camera.

35. System of claim 25 wherein each of said monitoring means and one or more of said detectors are combined in a camera.

36. System of claim 25 wherein said deviation signal comprises the time, location or time and location of said detected deviation.

37. System of claim 36 wherein said deviation signal comprises the location of said detected deviation.

38. A monitoring system for continuously monitoring a process for manufacturing a product comprising:

a plurality of monitoring means for continuously monitoring a pre-determined characteristic of the process and collecting monitored data, and each said monitoring means for monitoring and collecting data relative to said process;

data converting means for converting said collected data into digitized data;

digital data storage means for storing segments of said digitized data, said segments which cover the operations of said process over a predetermined period of time, said digitized data segments being stored such that as new digitized data is stored in a segment, earlier prior stored digitized data in said segment is removed from said segment to maintain said segment at or about a pre-determined length;

one or more deviation detectors for monitoring said pre-determined characteristic, and for detecting a deviation therefrom; and control means for controlling each of said monitoring means, said control means in communication with said digital data storage means and with said deviation detectors, wherein on receipt of a deviation signal said control means for extracting deviation digitized data corresponding to said detected deviation from said digital data storage means to form extracted deviation digitized data and said control means for controlling the display said extracted deviation digitized data.

39. System of claim 38 wherein said monitoring means is a camera.

40. System of claim 38 wherein each of said monitoring means and said data converting means are combined in a digital camera.

41. System of claim 38 wherein each of said monitoring means and said one or more detectors are combined in a camera.

42. System of claim 38 wherein said control means is one or more computers.

43. System of claim 38 wherein said deviation signal comprises the time, location or time and location of said detected deviation.

44. System of claim 43 wherein said deviation signal comprises the location of said detected deviation.

45. A monitoring system for continuously monitoring a process for manufacture of a product comprising:

a plurality of monitoring means for continuously monitoring a pre-determined characteristic of the process and collecting monitored data, each monitoring means addressing a different location of interest of said process, and each said monitoring means for monitoring and collecting data relative to said location;

digital converting means for converting said collected data into digitized data;

digital data storage means for storing segments of said digitized data, said segments which cover the operations of said process at a relevant location over a pre-determined period of time, said digitized data segments being stored such that as new digitized data is stored in a segment, earlier prior stored digitized data in said segment is removed from said segment to maintain said segment at or about a pre-determined length;

one or more deviation detectors for monitoring said pre-determined characteristics and for detecting a deviation therefrom; and control means for controlling each of said monitoring means, said control means in communication with said digital data storage means and with said deviation detectors, wherein on receipt of a deviation signal said control means for identifying a deviation digitized data corresponding to said deviation and extracting said identified deviation digitized data from said stored segments of digitized data in said digital data storage means to form extracted deviation digitized data, and said control means for controlling the display said extracted deviation digitized data.

46. System of claim 45 wherein said monitoring means is a camera.

47. System of claim 45 wherein each of said monitoring means and said data converting means are combined in a digital camera.

48. System of claim 45 wherein each of said monitoring means and said one or more detectors are combined in a camera.

49. System of claim 45 wherein each of said control means is one or more computers.

50. System of claim 45 wherein said deviation signal comprises the time, location or time and location of said detected deviation.

51. System of claim 50 wherein said deviation signal comprises the location of said detected deviation.

52. A monitoring system for continuously monitoring a process for the manufacture of a product comprising a continuous web of paper, said system comprising:

a plurality of monitoring means comprising a plurality of video cameras for monitoring a predetermined characteristic of the process and collecting monitored data, said cameras addressing locations of interest of said process and said cameras for producing video images relative to said locations;

digital data converting means for converting said video images into digitized video signals;

digital data storage means for receiving said digitized video signals and for storing segments of said digitized video signals, said segments which cover the operations of said process over a predetermined period of time, said digitized video signals being stored such that as new digitized video signals are stored in a segment, earlier prior stored digitized video signals in said segment are removed from said segment to maintain said segment at or about a pre-determined length; and control means for controlling each of said monitoring means, said control means comprising one or more computers, said control means for communicating with said digital data storage means and for communicating with one or more deviation detectors for detecting a deviation from said predetermined characteristics and for transmitting a deviation signal of said detected deviation to said control means, wherein on receipt of said deviation signal said control means for extracting a deviation digitized video signal from said segments stored in said digital data storage means and for controlling the display of said extracted deviation digitized video signal or an image thereof.

53. System of claim 52 wherein said system further comprises one or more video monitors for displaying said image of said extracted deviation digitized video signal and said control means for controlling the display of an image of said extracted deviation digitized video signal on one or more of said one or more video monitors.

54. System of claim 52 wherein said system further comprises one or more deviation detectors for monitoring said predetermined characteristics and for detecting deviations therefrom.

55. System of claim 54 wherein said monitoring means and said one or more detectors are combined in said video cameras.

56. System of claim 52 wherein said process is for printing said web of paper.

57. System of claim 52 wherein said process is for manufacturing said web of paper.

58. System of claim 57 wherein each predetermined characteristic is a characteristic of said product.

59. System of claim 58 wherein said predetermined characteristic is a continuity of said web.

60. System of claim 59 wherein said deviation is a break or hole in said web.

61. System of claim 60 wherein said deviation detectors further comprises one or more deviation detectors for monitoring said predetermined characteristics and for detecting deviations therefrom.

62. System of claims 61 whereas each of said monitoring means and said deviation detectors are combined in said video camera.

63. System of claim 61 wherein said deviation signal comprises the time, location or time and location of said detected deviation.

64. System of claim 52 wherein said predetermined characteristic is a characteristic of said product.

65. System of claim 52 wherein each of said monitoring means and said data converting means are combined in a digital camera.

66. System of claim 52 wherein said deviation signal comprises the time, location or time and location of said detected deviation.

* * * * *